United States Patent [19]

DeCaprio et al.

[11] Patent Number: 5,184,742
[45] Date of Patent: Feb. 9, 1993

[54] DEADENDER CAP FOR LUER FITTING

[75] Inventors: Michael J. DeCaprio, Camarillo; Stephen E. Rados, Oak View, both of Calif.

[73] Assignee: BOC Health Care, Inc., New Providence, N.J.

[21] Appl. No.: 539,641

[22] Filed: Jun. 18, 1990

[51] Int. Cl.$^5$ .............................................. B65D 39/08
[52] U.S. Cl. ...................................... 215/356; 215/364
[58] Field of Search ............... 215/320, 354, 355, 356, 215/364

[56] References Cited

U.S. PATENT DOCUMENTS

| | | | |
|---|---|---|---|
| 1,898,342 | 2/1933 | Cuthbert | 215/354 X |
| 1,937,000 | 11/1933 | Villanyi | 215/354 X |
| 3,199,704 | 8/1965 | Davidson | 215/354 X |
| 3,994,412 | 11/1976 | Difiglio | 220/266 |
| 4,340,148 | 7/1982 | Beckham | 215/329 |
| 4,573,980 | 3/1986 | Karrasch et al. | 604/256 |

Primary Examiner—Allan N. Shoap
Assistant Examiner—Nova Stucker
Attorney, Agent, or Firm—Roger M. Rathbun; Larry R. Cassett

[57] ABSTRACT

A deadender cap that is designed to be screwed into a standard medical Luer male thread connection to dead end that connection. The deadender cap is a one-piece molded construction having an internal tapered projection that fits within the open passages of the male Luer connection a predetermined distance when the deadender cap is tightened into position, thus liquid within the open passage is forced outwardly and then as the deadender cap is tightened and no air bubbles are formed.

1 Claim, 2 Drawing Sheets

DEADENDER CAP FOR LUER FITTING

BACKGROUND OF THE INVENTION

This invention relates to disposable medical blood pressure measuring devices that are utilized with in vivo catheters to measure and record the blood pressure of a patient. Basically, in vivo blood pressure monitoring is widely used in hospitals and includes a liquid filled catheter system that is introduced into the particular blood vessel to be monitored. The open end of the liquid filled catheter thus is placed within the patient's blood vessel and a continuous column of liquid takes up the space between that catheter end and a pressure transducer. The blood pressure may therefore be directly measured by the transducer remote from the patient by measuring the fluctuations of pressure at the external end of the liquid column.

Typically, such pressure transducers comprise strain guages in the form of cantilever beams, for example in U.S. Pat. No. 4,545,389 and 4,683,894, or may comprise tiny silicon chips with a moveable diaphragm etched into the chip. One side of the diaphragm or cantelever beam is subject to the fluctuating pressures transmitted by the column of liquid while the other side is vented to atmosphere. The transducer then electronically senses the amount of flexing of the diaphragm or chip and translates the amount of flex into an electrical signal.

It is, obviously, of extreme importance that the column of liquid filling the tubing and catheter between the pressure transducer and the open end of the catheter be solid, that is, free of air or other gas bubbles.

Any such air bubbles in the liquid column creates frequency degrading, erroneous pressure waveforms and/or misleading diastolic and systolic pressure measurements. Certainly, in the hospital environment, and particularly, due to the major use of invivo blood pressure sensing in the operating room, or cath lab, accuracy and fidelity of signal is of extreme importance.

In setting up such invivo blood pressure systems, it is standard to flush the system, including the patient side of the pressure transducer with a sterile liquid to insure that the transducer is completely filled with liquid. A syringe connected to a stopcock located at one end of the transducer normally is used to force liquid through the stopcock and into a passageway passing through the transducer and out a downstream opening on the opposite side of the transducer. The preferred stopcock is a two position valve alternating between one position where the syringe communicates with the transducer passageway and another position when the line containing the column of liquid to the patient communicates with the transducer passageway. When sufficient liquid has been flushed out the downstream opening, a cap, known as a deadender cap is tightened to close the downstream opening of the transducer. The stopcock is then moved to its position that shuts off the communication with the syringe and opens the patient line to the transducer.

In many such pressure transducers, the downstream opening is a standard male Luer lock fitting, which conforms to certain medical uniform specifications and which ends in a fairly flat, circular opening.

In present deadender caps, a flat surface is formed in the closed end of the caps. One disadvantage of such deadender caps has been discovered to be the trapping of minute to large amounts of air as they are closed tight by engagement of the threaded lock. The air is trapped by engagement of the Luer tapers or in moving the flat surface into abutment with the circular opening to deadend the downstream opening. A recurring problem has thus arisen in that a bubble is created and which readily enters the transducer itself since, in use, the transducer may often be inverted or moved into various positions that would induce a bubble to progress along the liquid filled transducer passageways causing the aforedescribed difficulties in the transducer use and accuracy.

SUMMARY OF THE INVENTION

In accordance with the present invention, a deadender cap is provided for use with a male Luer lock fitting and which may be used to close the downstream opening after flushing liquid through the pressure transducer. The deadender cap is adapted to be threaded to the male Luer lock fitting so as to be readily tightened against the circular opening in that fitting. A tapered projection is molded into the deadender cap that is of a predetermined length and taper such that the projection actually enters the Luer lock circular opening and, as the cap is tightened, displaces excess liquid out of the passageway in the male Luer fitting. By such means, the cap prevents the formation of an air pocket in or at the end of the Luer passageway.

DESCRIPTION OF THE PREFERRED EMBODIMENT

Figure 1:
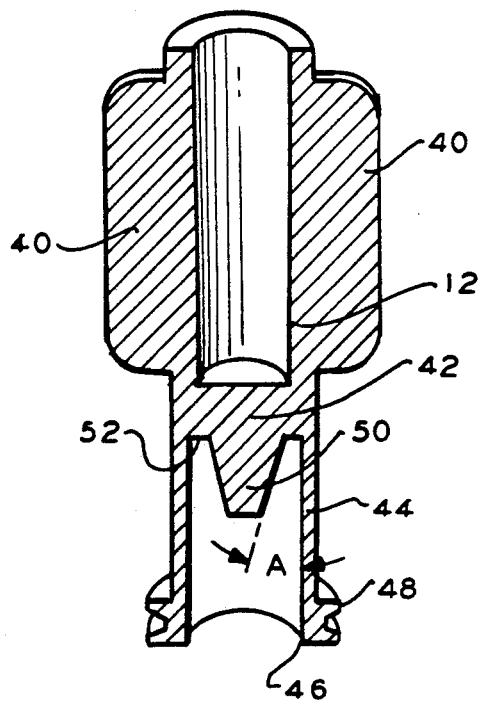
FIG. 1 is a perspective view of a disposable pressure transducer in the process of being flushed and including a deadender cap constructed in accordance with the present invention.

Referring now to FIG. 1, there is shown a perspective view of a disposable pressure transducer 10 having affixed thereto, a deadender cap 12 constructed in accordance with the present invention. As will be explained, the disposable pressure transducer 10 may be of conventional design, such as shown and described in the aforementioned U.S. Pat. Nos. 4,545,389 and 4,683,894 and includes male Luer fittings 14 and 16 which are standardized medical fittings having certain dimensions, threads and the like.

Typical of such disposable pressure transducers 10 is the inclusion of electrical cable 18 ending in a special plug 20 for connection to a monitor for providing a visual readout of the various detected parameters such as systolic and diastolic blood pressures and include a wave form of the blood pressure plythsmograph.

As shown in FIG. 1, a stopcock 21 is connected to male Luer fitting 16 and in turn, connected to stopcock 21 are a syringe 22 and a patient line 23. Stopcock 21 is moveable between two positions by lever 24. In one position, as shown in FIG. 1, the syringe 22 communicates through stopcock 21 to a passageway (not shown in FIG. 1) that extends through the disposable pressure transducer 10 to male Luer fitting 16. In the other position of stopcock 21, the patient line 23, which contains the column of liquid leading to the patient, is in communication with the passageway of disposable pressure transducer and the syringe is isolated from such communication.

Accordingly, to insure that the disposable pressure transducer 10 is filled with liquid, the syringe 22 is prefilled with a sterile liquid. The stopcock is placed in the position shown in FIG. 1 where the syringe 22 communicates through stopcock 21 and syringe 21 is depressed to force liquid through the passageway of disposable pressure transducer 10 to be discharged through the male Luer fitting 14 at the opposite end of the passageway, thereby flushing liquid through the disposable pressure transducer 10.

The person carrying out the filling procedure can thus observe liquid being discharged through male Luer fitting 14 and tighten deadender cap 12 when sufficient liquid has been noted to insure the observer that all passageways through the disposable pressure transducer 10 have been filled with liquid. Stopcock 21 is then turned to its other position to isolate the syringe 22 from disposable pressure transducer 10 and patient line 23 is then in communication with the passageway therein. The syringe 22 can then be removed.

Figure 5:
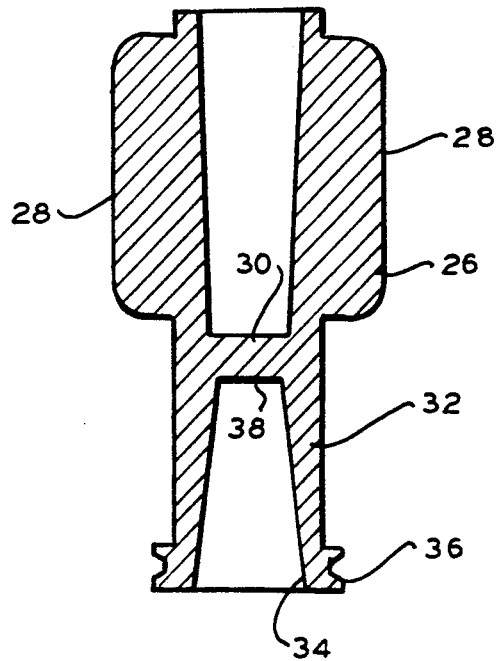
FIG. 5 is a side cross sectional view of a typical prior art deadender cap.

Turning now to FIG. 5, there is shown a side cross sectional view of a typical prior art deadender cap 26. As shown, deadender cap 26 is a one piece injection molded unit of a high impact plastic such as acrylonitrile-butadiene-styrene (ABS) and includes a pair of wings 28 to be grasped by a user for twisting the deadender cap 26 to install or remove the same.

Deadender cap 26 also includes a separation wall 30 and a cylindrical (or circular) hub 32 that has a Luer taper and which extends outwardly from separation wall 30 terminating in an open end 34. External threads 36 are formed on the cylindrical hub 32 adjacent the open end 34 for interfitting with the threads of a standard male Luer fitting, the purpose of which will become apparent during the later explanation of the subject invention.

It should be noted that the internal surface 38 of the separation wall 30 within cylindrical hub 3 is a flat surface and a dead space is formed when the prior art deadender cap 26 is mated onto the tapered male Luer fitting where air may become entrapped.

Figure 2:
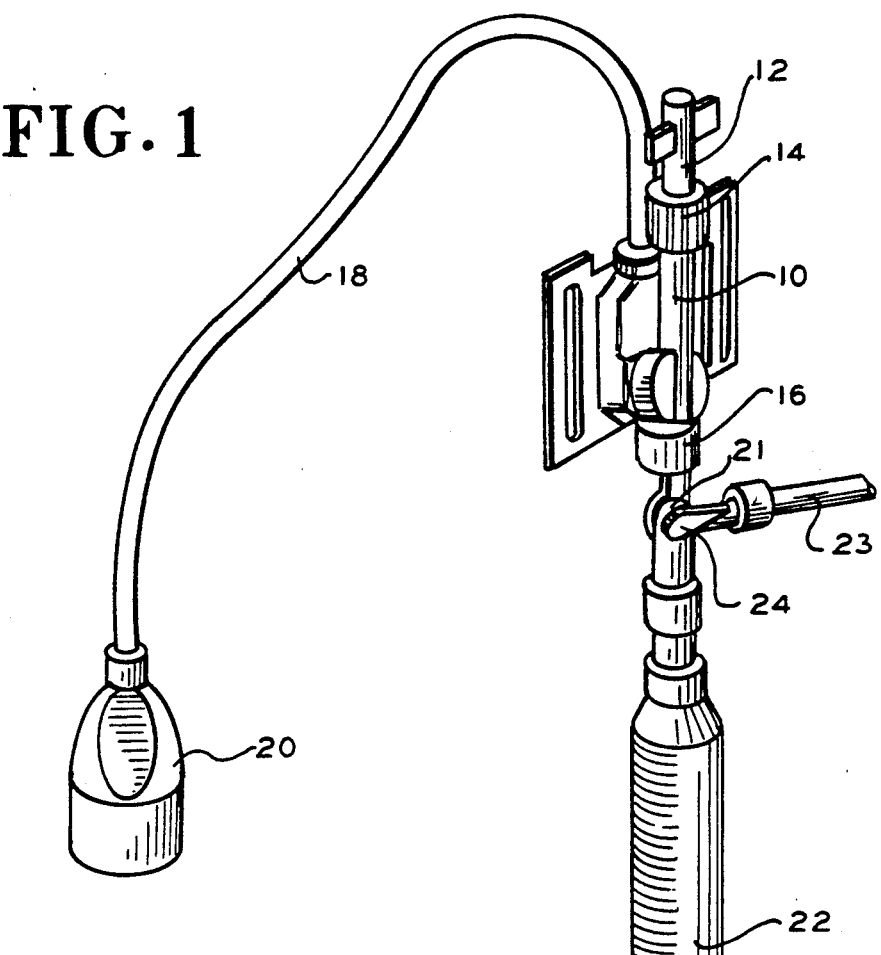
FIG. 2 is a perspective view in cross section of the deadender cap of FIG. 1.

Turning now to FIG. 2, there is shown a perspective view, in cross section, of a deadender cap 12 constructed in accordance with the present invention. The deadender cap 12 is again of a one piece molded plastic construction of ABS or similar material. A pair of wings 40 extend outwardly approximately 180° apart to enable the user to easily grasp the deadender cap 12 for rotating it in either direction.

Deadender cap 12 further includes a separator wall 42 and a cylindrical hub 44 that is not a Luer taper extending forwardly from the separator wall 42 terminating in an open end 46.

On the exterior of cylindrical hub 44 are threads 48 adjacent open end 46, the purpose of which will be explained.

Within the cylindrical hub 44 is a tapered projection 50 that extends outwardly from separation wall 42 toward open end 46 and tapers inwardly a predetermined amount. An annular surface 52 is formed on separator wall 42 surrounding the tapered projection 50.

The deadender cap 12 is molded having certain fairly precise dimensions. As an example, the external threads 48 and internal diameter of the cylindrical hub 44 are, of course, dimensioned within specific tolerances in order to attach to the standard male Luer fitting that is set by ANSI standards for medical applications. Thus the deadender cap 12 can be standardized so as to fit onto any medical Luer fitting of the particular size concerned. Other critical dimensions, as well become apparently include the amount of taper of the tapered projection 50 and the depth of the cylindrical hub 44, that is, the distance from the open end 46 of cylindrical hub 44 to the annular surface 52. The angle of taper of tapered projection 50 shown as A in FIG. 2 is preferably from about 5 to about 8 degrees.

Figure 3:
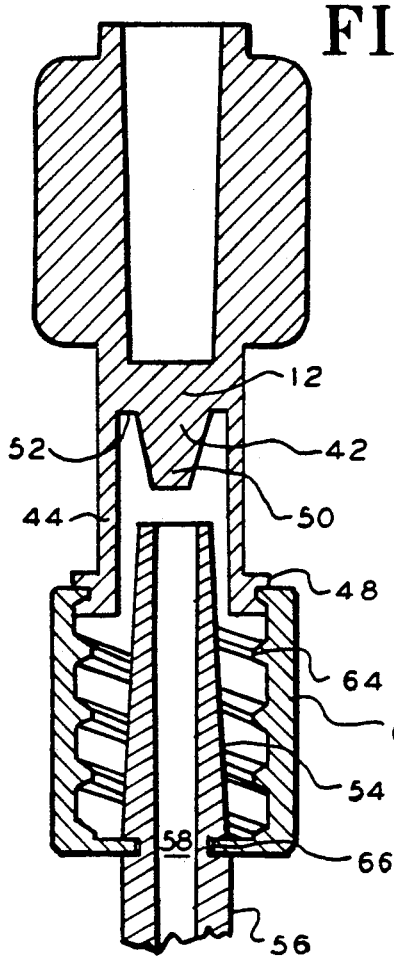
FIG. 3 is a side cross sectional view of the deadender cap of FIG. 2 show in loose engagement with a male Luer lock fitting.

Turning now to FIG. 3, there is shown a side cross sectional view of a deadender cap 12 loosely affixed to a male Luer lock fitting 54. Again, the male Luer lock fitting 54 is a standard fitting dimensionally and includes a cylindrical tubing 56 containing a passageway 58 and tapering down in accordance with Luer standards to end in a flat circular opening 60. A threaded fitting 62 surrounds cylindrical tubing 56 and has internal threads 64 formed therein dimensioned to accept the threads 48 of deadender cap 12. A cylindrical flange 66 interfits inside threaded fitting 62 and holds threaded fitting 62 to the end of cylindrical tubing 56.

As may now be seen, the internal diameter of cylindrical hub 44 fits over the tapered end of cylindrical tubing 56 and threads 48 of the deadender cap 12 engage the internal threads 64 of threaded fitting 62. By rotating threaded fitting 62, the deadender cap 12 can thus be affixed to or removed from male Luer fitting 54.

Figure 4:
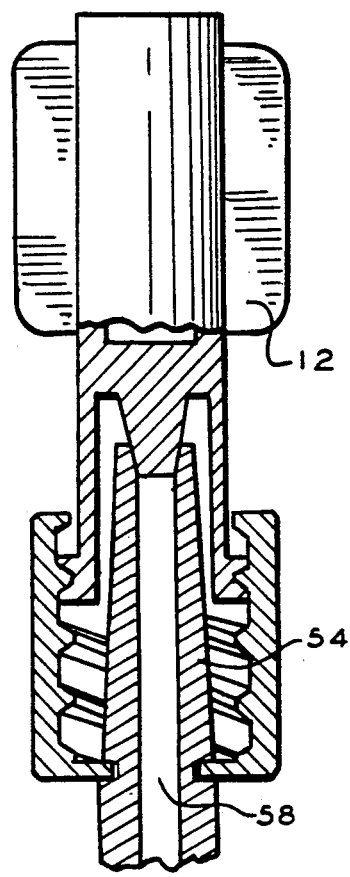
FIG. 4 is a side cross sectional view of the deadender cap of FIG. 2 tightened against the male Luer fitting to prevent flow therefrom.

Turning finally to FIG. 4, there is shown a side cross sectional view of a deadender cap 12 fully engaging a male Luer fitting 54. Due to the specific predetermined dimensions of deadender cap 12, it can be seen that when the deadender cap 12 is fully tightened on to male Luer fitting 54, the tapered projection 50 fits within and closes passageway 58.

Taking now, FIG. 1 along with FIGS. 3 and 4, it can be seen that the disposable pressure transducer 10 is flushed with liquid from syringe 22 through stopcock 21 and which liquid is flushed through and out passageway 58 when deadender cap 12 is in the FIG. 3 position. The liquid readily passes along the threads between cylindrical tubing 56 and threaded fitting 62 to the outside environment.

When the user determines that sufficient liquid and air has leaked out past deadender cap 12, the deadender cap 12 is tightened by engagement of the respective threads 64 and 48 to the position of FIG. 4.

In carrying out such tightening, the liquid passing out of passageway 58 through flat opening 60 is halted when the syringe movement is terminated and the stopcock is moved to its position isolating syringe 22. That liquid forms a maniscus over flat circular opening 60. As deadender cap 12 is thereafter tightened, the tapered projection 50 enters the passageway 58 and forces excess liquid out from flat circular opening when the tapered projection 50 finally seats within and closes passageway 58 excess liquid has been exhausted and the remaining liquid sealed tightly within passageway 58. Thus there is no dead air space that can cause the formation of a bubble. To the contrary, in the prior art deadender cap 26, the flat internal surface 38 would leave a tiny void or dead space creating a bubble.

What is claimed is:

1. In combination, a standard male Luer fitting having internal threads and an internal cylindrical passageway, and a deadender cap affixed to said standard male Luer fitting, said deadender cap having an intermediate wall, a cylindrical hub extending from said intermediate wall a predetermined distance and having an open end, said cylindrical hub having external threads engaging said internal threads of said standard male Luer fitting, a projection integrally molded to said intermediate wall and extending outwardly therefrom within said cylindrical hub, said projection being tapered inwardly along its length extending outwardly from said intermediate wall to enter and close said cylindrical passageway of said standard male Luer fitting.

* * * * *